United States Patent
Hesse et al.

(10) Patent No.: US 6,448,457 B1
(45) Date of Patent: Sep. 10, 2002

(54) METHOD FOR HYDROGENATING CARBONYL COMPOUNDS

(75) Inventors: Michael Hesse, Worms; Detlef Kratz, Heidelberg; Gerhard Schulz, Ludwigshafen; Marc Walter, Frankenthal; Manfred Sauerwald, Meckenheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/623,172

(22) PCT Filed: Mar. 5, 1999

(86) PCT No.: PCT/EP99/01427

§ 371 (c)(1), (2), (4) Date: Aug. 29, 2000

(87) PCT Pub. No.: WO99/44974

PCT Pub. Date: Sep. 10, 1999

(30) Foreign Application Priority Data

Mar. 5, 1998 (DE) .......................................... 198 09 418

(51) Int. Cl.⁷ .............................................. C07C 27/04
(52) U.S. Cl. ........................ 568/885; 568/903; 502/345; 502/346; 502/350
(58) Field of Search ................................. 568/885, 903; 502/345, 346, 350

(56) References Cited

U.S. PATENT DOCUMENTS

| 3,803,055 A | 4/1974 | Reich ........................ 252/454 |
| 3,886,219 A | 5/1975 | Reich ........................ 260/638 |
| 4,386,018 A | 5/1983 | Merger et al. .............. 252/465 |
| 4,386,219 A | 5/1983 | Merger et al. .............. 568/853 |
| 4,918,248 A | 4/1990 | Hattori et al. .............. 568/885 |
| 5,217,937 A | 6/1993 | Schneider et al. .......... 502/242 |

FOREIGN PATENT DOCUMENTS

| DE | 10 30 939 | 1/1999 |
| EP | 484 800 | 5/1992 |

*Primary Examiner*—Sreeni Padmanabhan
(74) *Attorney, Agent, or Firm*—Keil & Weinkauf

(57) ABSTRACT

A process for the catalytic hydrogenation of a carbonyl compound or of a mixture of two or more carbonyl compounds in the presence of a catalyst which comprises an inorganic support containing $TiO_2$, and as active component copper or a mixture of copper and at least one of the metals selected from the group of zinc, aluminum, cerium, a noble metal and a group VIII metal, wherein the copper surface area does not exceed 10 $m^2/g$.

11 Claims, No Drawings

METHOD FOR HYDROGENATING CARBONYL COMPOUNDS

This application is the U.S. National Stage Application of PCT/EP99/01427 filed Mar. 3, 1999 now WO 99/44974 published Sep. 10, 1999.

The invention relates to a process for the catalytic hydrogenation of carbonyl compounds in the presence of a copper catalyst, to the copper catalyst as such and to a process for its preparation.

Catalytic hydrogenation of carbonyl compounds, such as aldehydes, to prepare simple and functionalized alcohols occupies an important place in the production sequences in the basic chemicals industry. This is particularly true of the hydrogenation of aldehydes which can be obtained by the oxo synthesis or the aldol reaction.

Catalytic hydrogenation of aldehydes in a suspension or fixed bed procedure has been known for a long time. Industrial systems operate almost exclusively with fixed bed reactors.

The fixed bed catalysts used, beside catalysts of the Raney type (DE-A 197 30 939), are in particular supported catalysts, for example copper, nickel or noble metal catalysts.

DE-A 16 43 856 describes the hydrogenation of aldehydes to alcohols on combined Cu/Ni supported catalysts in the gas phase. The supports used in this case must be neutralized with alkalis before use.

DE-A 40 37 729 describes a Cu/Cr system which is employed as catalyst for hyrdogenating fatty acids or fatty acid esters but which is problematic in terms of environmental pollution owing to the chromium component. In addition, these catalysts require relatively drastic reaction conditions in the hydrogenation, which may lead to increased formation of unwanted by-products.

Supported catalysts which do not contain the objectionable chromium are described in EP-A 0 044 444. Although the Cu hydrogenation catalysts supported on $Al_2O_3$ and employed in the process described therein for preparing propanediol show a high initial activity, their properties are unsatisfactory in terms of their useful lives.

EP-A 0 484 800 discloses the use of Cu/Zn catalysts supported on $ZrO_2$ for hydrogenating hydroxypivalaldehyde to neopentyl glycol.

U.S. Pat. No. 4 918,248 discloses the use of Cu/Zn catalysts supported on $TiO_2$, but the use thereof is restricted exclusively to the hydrogenation of carboxylic esters.

It is an object of the present invention to provide a process for the catalytic hydrogenation of carbonyl compounds employing a catalyst which is easy to prepare industrially, has high mechanical stability under the reaction conditions occurring in said process, and makes high conversions and selectivities possible.

We have found that this object is achieved by an embodiment of tableting in which a dried powder which comprises the support material and the active component is mixed with metallic Cu powder in addition to a conventional tableting aid such as graphite, leading both to particularly easy tableting and to high activities and selectivities, and to high catalyst stability.

An outstanding property of the catalyst tablets obtained in this way is the exceptional mechanical strength. It is only on addition of metallic Cu powder used according to the invention that the tablets acquire the mechanical stability necessary to produce with the chosen support material a catalyst which can be employed usefully under the reaction conditions of catalytic hydrogenation.

Accordingly, the object has been achieved by a process for the catalytic hydrogenation of a carbonyl compound or of a mixture of two or more carbonyl compounds in the presence of a catalyst which comprises an inorganic support containing $TiO_2$, and as active component copper or a mixture of copper and at least one of the metals selected from the group of zinc, aluminum, cerium, a noble metal and a group VIII metal, wherein the specific copper surface area does not exceed 10 $m^2/g$.

The support preferably used is $TiO_2$ or a mixture of $TiO_2$ and $Al_2O_3$ or a mixture of $TiO_2$ and $ZrO_2$ or a mixture of $TiO_2$, $Al_2O_3$ and $ZrO_2$, particularly preferably $TiO_2$.

The catalysts used in the process according to the invention is distinguished in that the copper active component is applied to the support material used, there being no restrictions whatever on the method of application.

The following methods of application are suitable in particular:

a) Application of a copper salt solution in one or more impregnation stages to a prefabricated inorganic support. Following the impregnation, the support is dried and, where appropriate, calcined.

a1) The impregnation can take place by the "incipient wetness" method, in which the support is moistened with the impregnation solution to no further than saturation according to its water-uptake capacity. The impregnation can, however, also take place in a supernatant solution.

a2) In multistage impregnation processes, it is expedient to dry and, where appropriate, to calcine between individual impregnation steps. Multistage impregnation is advantageously to be used particularly when the support is to be loaded with a relatively large amount of copper.

a3) The inorganic support material is preferably employed as preshaped mass for the impregnation, for example as powder, beads, extrudates or tablets. The use of a powder is particularly preferred.

a4) Concentrated aqueous ammonia is preferably employed as solvent for copper salts.

b) Precipitation of a copper salt solution onto a prefabricated inert inorganic support. The latter is, in a particularly preferred embodiment, in the form of a powder in an aqueous suspension.

b1) In one embodiment (i) a copper salt solution is precipitated, preferably with sodium carbonate solution. An aqueous suspension of the support material is present in the recipient vessel.

b2) In another embodiment (ii), the precipitated catalyst can be prepared in a two-stage process. This entails, in a first stage, a powder being prepared and dried as stated in a). This powder is transferred into an aqueous suspension and employed in the recipient vessel equivalent to the description in embodiment (i).

Precipitates resulting from a) or b) are filtered in a conventional way and preferably washed free of alkali.

Both the final products from a) and those from b) are dried at temperatures of from 50 to 150° C., preferably at 120° C., and then, where appropriate, calcined, preferably for 2 hours, in general at 200 to 400° C., in particular at 200 to 220° C.

The starting substances which can be used for a) and/or b) are in principle all Cu(I) and/or Cu(II) salts soluble in the solvents used for the application, for example sulfates, nitrates, chlorides, carbonates, acetate, oxalates or ammonium complexes. Copper carbonate is particularly preferably employed for a) processes and copper nitrate is particularly preferably employed for b) processes.

In the process according to the invention, the dried powder described above is preferably shaped to tablets or similar shaped articles. A tableting aid for the shaping process is added in the form of graphite, preferably in an amount of 3% by weight based on the weight of the dried powder.

A further additive for preparing the catalyst, in addition to the powder described above and to graphite, is added in the form of metallic Cu powder. 5 to 40% by weight of metallic Cu powder, in particular 15 to 20% by weight, are preferably added, based on the weight of the dried powder described above.

Accordingly, the present invention also relates to a catalyst which comprises an inorganic support which contains $TiO_2$, and as active component copper or a mixture of copper with at least one of the metals selected from the group of zinc, aluminum, cerium, a noble metal and a group VIII metal, obtainable by a process which comprises a tableting step, wherein metallic copper powder is added in the tableting.

The tableted articles according to the invention are heat-treated at 300 to 600° C., in particular at 330 to 350° C., preferably for 2 hours. This novel type of tableting process makes it particularly easy to shape the powder to tablets, compared with the exclusive use of graphite as tableting aid in conventional processes, and provides very chemically and mechanically stable catalysts.

The parameters of "hardness" and "attrition" can be determined as follows. To determine the cutting hardness, samples are divided with a cutter. The force which must be applied to the cutter in order to divide the sample is referred to as the cutting hardness of the material.

The fracture hardness of spherical samples is determined by placing the spheres under a punch with a defined area and then moving the punch against the sphere until it fractures. The pressure it is necessary to exert with the punch on the sample to achieve fracture is referred to as the fracture hardness.

The attrition is determined using a vibrating mill. This entails catalyst material of a particular particle size range being agitated together with porcelain beads in a container at a high speed of rotation for a particular time. The catalyst is then sieved again. The loss in weight in % is then referred to as the attrition, as described in Chapter 6 in J.-F. Le Page et al., "Applied Heterogeneous Catalysis", Editions Technip, Paris (1987).

The calcined catalyst is activated either before or after installation in the reactor.

If the catalyst is to be used in its reduced form, it is installed in the reactor and charged with the hydrogenation solution directly under a pressure of hydrogen. On use in the oxide form, before charging with the hydrogenation solution the catalyst is previously reduced with reducing gases, for example hydrogen, preferably hydrogen/inert gas mixtures, in particular hydrogen/nitrogen mixtures, at temperatures from 100 to 300, preferably from 150 to 250, in particular from 180 to 240° C. A mixture with a hydrogen content of from 1 to 100% by volume is preferably used in these cases.

A characteristic variable of the catalysts according to the invention is their specific copper surface area. It is calculated from the $N_2O$ consumption found in a heated sample of the catalyst due to oxidation of surface copper atoms with gaseous $N_2O$.

For this purpose, the sample is first treated with 10 mbar of hydrogen at a temperature of 240° C. for 4 hours. The sample is subsequently evacuated to a pressure below $10^{-3}$ mbar and then treated with 30 mbar of $H_2$ for 3 hours, subsequently evacuated to less than $10^{-3}$ mbar again, treated with 100 mbar of $H_2$ for 3 hours, once again evacuated to less than 10–3 mbar and finally treated again with 200 mbar of $H_2$ for 3 hours, each treatment with hydrogen being carried out at a temperature of 240° C.

In a second stage, the sample is exposed to $N_2O$ under a pressure of 266 mbar at a temperature of 70° C. for 2 hours, during which $N_2O$ is observed to decompose on the sample. The sample is subsequently evacuated to less than $10^{-3}$ mbar, and then the increase in the weight of the catalyst as a result of the formation of copper oxide on the surface thereof is determined.

The specific copper surface area measured in this way for the catalysts prepared according to the invention generally does not exceed 10 $m^2/g$, and is preferably 0.1 to 10 $m^2/g$, and is further preferably in the range from 0.5 to 7 $m^2/g$, in particular in the range from 0.5 to 5 $m^2/g$.

Accordingly, the present invention also relates to a catalyst which comprises an inorganic support which contains $TiO_2$, and as active component copper or a mixture of copper with at least one of the metals selected from the group of zinc, aluminum, cerium, a noble metal and a group VIII metal, wherein the copper surface area does not exceed 10 $m^2/g$.

The present invention accordingly also relates to a process for preparing a catalyst which comprises an inorganic support which contains $TiO_2$, and as active component copper or a mixture of copper with at least one of the metals selected from the group of zinc, aluminum, cerium, a noble metal and a group VIII metal, and whose copper surface area does not exceed 10 $m^2/g$, which comprises a tableting, wherein metallic copper powder is added in the tableting.

The catalysts prepared according to the invention are preferably employed for fixed-bed hydrogenation. However, the embodiment as fluidized bed reaction with catalyst material moving upwards and downwards is likewise possible. The hydrogenation can be carried out in the gas phase or in the liquid phase. The hydrogenation is preferably carried out in liquid phase, for example in a downflow or upflow procedure.

With a downflow procedure, the liquid precursor containing the carbonyl compound to be hydrogenated is allowed to trickle over the catalyst bed arranged in the reactor, which is under a pressure of hydrogen, with a thin film of liquid forming on the catalyst. By contrast, with an upflow procedure, hydrogen gas is passed into the reactor through which the liquid reaction mixture flows, with the hydrogen passing through the catalyst bed in ascending gas bubbles.

In one embodiment, the solution to be hydrogenated is pumped straight through the catalyst bed. In another embodiment of the process according to the invention, part of the product after passing through the reactor is continuously taken off as product stream and, where appropriate, passed through a second reactor as defined above. The other part of the product is fed to the reactor again together with fresh precursor containing the carbonyl compound. This procedure is referred to as recycle procedure below.

If the downflow procedure is chosen as embodiment of the process according to the invention, the recycle procedure is preferred. It is further preferred to use a main reactor and second reactor in the recycle procedure.

The process according to the invention is suitable for the hydrogenation of carbonyl compounds such as aldehydes and ketones to the corresponding alcohols, with aliphatic and cycloaliphatic, saturated and unsaturated carbonyl compounds being preferred. With aromatic carbonyl compounds there may be formation of unwanted by-products through hydrogenation of the aromatic nucleus. The carbonyl compounds may contain other functional groups such as hydroxyl or amino groups. Unsaturated "carbonyl compounds" are usually hydrogenated to the corresponding saturated alcohols. The term "carbonyl compounds" as used for the purpose of the invention comprises all compounds which have a C=O group, including carboxylic acids and derivatives thereof. It is, of course, also possible to hydrogenate mixtures of two or more than two carbonyl compounds together. A further possibility is also for the individual carbonyl compound to be hydrogenated to contain more than one carbonyl group.

The process according to the invention is preferably employed for hydrogenating aliphatic aldehydes, hydroxy aldehydes, ketones, acids, esters, anhydrides, lactones and sugars.

Preferred aliphatic aldehydes are branched and unbranched, saturated and/or unsaturated aliphatic $C_2$–$C_{30}$-aldehydes like those obtainable, for example, by oxo synthesis from linear or branched olefins with internal or terminal double bond. A further possibility is also to hydrogenate oligomeric compounds which also contain more than 30 carbonyl groups.

Examples of aliphatic aldehydes which may be mentioned are:

formaldehyde, propionaldehyde, n-butyraldehyde, isobutyraldehyde, valeraldehyde, 2-methylbutyraldehyde, 3-methylbutyraldehyde (isovaleraldehyde), 2,2-dimethylpropionaldehyde (pivalaldehyde), caproaldehyde, 2-methylvaleraldehyde, 3-methylvaleraldehyde, 4-methylvaleraldehyde, 2-ethylbutyraldehyde, 2,2-dimethylbutyraldehyde, 3,3-dimethylbutyraldehyde, caprylaldehyde, capraldehyde, glutaraldehyde.

Besides the short-chain aldehydes mentioned, also particularly suitable are long-chain aliphatic aldehydes like those which can be obtained, for example, by oxo synthesis from linear α-olefins.

Enalization products are particularly preferred, such as 2-ethylhexenal, 2-methylpentenal, 2,4-diethyloctenal or 2,4-dimethylheptenal.

Preferred hydroxy aldehydes are $C_3$–$C_{12}$-hydroxy aldehydes like those obtainable, for example, by aldol reaction from aliphatic and cycloaliphatic aldehydes and ketones with themselves or formaldehyde. Examples are 3-hydroxypropanal, dimethylolethanal, trimethylolethanal (pentaerythrital), 3-hydroxybutanal (acetaldol), 3-hydroxy-2-ethylhexanal (butyraldol), 3-hydroxy-2-methylpentanal (propionaldol), 2-methylolpropanal, 2,2-dimethylolpropanal, 3-hydroxy-2-methyl-butanal, 3-hydroxypentanal, 2-methylolbutanal, 2,2-dimethylolbutanal, hydroxypivalaldehyde. Hydroxypivalaldehyde (HPA) and dimethylolbutanal (DMB) are particularly preferred.

Preferred ketones are acetone, butanone, 2-pentanone, 3-pentanone, 2-hexanone, 3-hexanone, cyclohexanone, isophorone, methyl isobutyl ketone, mesityl oxide, acetophenone, propiophenone, benzophenone, benzalacetone, dibenzalacetone, benzalacetophenone, 2,3-butanedione, 2,4-pentanedione, 2,5-hexanedione and methyl vinyl ketone.

It is also possible to convert carboxylic acids and derivatives thereof, preferably those having 1–20 C atoms. The following should be mentioned in particular:

carboxylic acids such as formic acid, acetic acid, propionic acid, butyric acid, isobutyric acid, n-valeric acid, trimethylacetic acid ("pivalic acid"), caproic acid, enanthic acid, caprylic acid, capric acid, lauric acid, myristic acid, palmitic acid, stearic acid, acrylic acid, methacrylic acid, oleic acid, elaidic acid, linoleic acid, linolenic acid, cyclohexanecarboxylic acid, benzoic acid, phenylacetic acid, o-toluyic acid, m-toluylic acid, p-toluylic acid, o-chlorobenzoic acid, p-chlorobenzoic acid, o-nitrobenzoic acid, p-nitrobenzoic acid, salicylic acid, p-hydroxybenzoic acid, anthranilic acid, p-aminobenzoic acid, oxalic acid, malonic acid, succinic acid, glutaric acid, adipic acid, pimelic acid, suberic acid, azelaic acid, sebacic acid, maleic acid, fumaric acid, phthalic acid, isophthalic acid, terephthalic acid;

carbonyl halides such as the chlorides or bromides of the abovementioned carboxylic acids, especially acetyl chloride or bromide, stearyl chloride or bromide and benzoyl chloride or bromide, which are, in particular, dehalogenated;

carboxylic esters such as the $C_1$–$C_{10}$-alkyl esters of the abovementioned carboxylic acids, in particular methyl formate, ethyl acetate, butyl butyrate, dimethyl terephthalate, dimethyl adipate, dimethyl maleate, methyl (meth)acrylate, butyrolactone, caprolactone and polycarboxylic esters such as polyacrylic and polymethacrylic esters and their copolymers and polyesters such as polymethylmethacrylate, terephthalic esters and other engineering plastics, in this case hydrogenolyses, i.e. the conversion of esters to the corresponding acids and alcohols, being carried out in particular;

fats;

carboxylic anhydrides such as the anhydrides of the abovementioned carboxylic acids, especially acetic anhydride, propionic anhydride, benzoic anhydride and maleic anhydride;

carboxamides such as formamide, acetamide, propionamide, stearamide, terephthalamide.

It is also possible to convert hydroxy carboxylic acids such as lactic, malic, tartaric or citric acid, or amino acids such as glycine, alanine, proline and arginine, and peptides.

The process according to the invention is particularly preferably employed for hydrogenating aldehydes and hydroxy aldehydes.

The carbonyl compound to be hydrogenated can be fed into the hydrogenation reactor alone or as mixture with the product of the hydrogenation, in which case this can take place in undiluted form or with use of additional solvent. Particularly suitable additional solvents are water, alcohols such as methanol, ethanol and the alcohol produced under the reaction conditions. Preferred solvents are water, THF, NMP, and ethers such as dimethyl and diethyl ethers, MTBE, and water is particularly preferred.

The hydrogenation in both the upflow and the downflow procedure, each preferably being carried out as recycle procedure, is generally carried out at a temperature from 50 to 250° C., preferably at 70 to 200° C., particularly preferably at 100 to 140° C., under a pressure of from 15 to 250 bar, preferably 20 to 200 bar, particularly preferably 25 to 100 bar.

High conversions and selectivities are obtained in the process according to the invention, and the catalysts show high chemical stability in the presence of the reaction mixture. With identical support material, the catalysts prepared according to the invention show, by comparison with catalysts prepared according to the prior art, both easier shaping to tablets and, after the heat treatment of the tableted articles, distinctly greater mechanical stability, both in the oxidized and in the reduced state, resulting in the process according to the invention being distinguished by being particularly economical.

The invention is explained in detail in the following examples.

EXAMPLES

Catalyst preparation

All the percentage data indicated in this subsection represent percentages by weight unless noted otherwise. The copper oxide crystallite sizes indicated for the individual catalysts were determined by XRD. The indicated percentage compositions are based on the oxide constituents of the finished catalysts.

Catalyst A (comparison)

Catalyst A was prepared by precipitating a solution of copper and aluminum nitrate with sodium carbonate solution. The resulting precipitate was filtered off, washed and dried at 120° C. The dried powder was calcined at 250° C. for 2 hours and then compressed with 3% graphite to tablets with a diameter of 5 mm. These tablets were heat treated at 580° C. for 2 hours. The finished catalyst contained 53% CuO and 47% $Al_2O_3$, with a tap density of 1090 g/l, a BET surface area of 101 $m^2/g$ or 110090 $m^2/l$, a copper surface area of 11.5 $m^2/g$ or 11445 $m^2/l$, a copper oxide crystallite size of 15.0 nm and a water uptake of 0.41 ml/g or 447 ml/l.

Catalyst B (comparison)

Catalyst B was prepared by impregnating $SiO_2$ beads with a diameter of 3 to 5 mm with a solution of copper carbonate in concentrated aqueous ammonia. Impregnation took place in supernatant solution for 15 min. The impregnated beads were dried at 120° C. for 5 hours and then calcined at 250° C. for 2 hours. These impregnation and calcining steps were repeated. The finished catalyst contained 25.6% CuO and 74.4% $SiO_2$, with a tap density of 605 g/l, a BET surface area of 212 $m^2/g$ or 128260 $m^2/l$, a copper surface area of 9.8 $m^2/g$ or 5929 $m^2/l$, a copper oxide crystallite size of 2.5 nm and a water uptake of 0.54 ml/g or 327 ml/l.

Catalyst C (comparison)

Catalyst C was prepared by impregnating $TiO_2$ powder with a solution of copper carbonate in concentrated aqueous ammonia. Impregnation took place first at room temperature and then at 100° C. The powder impregnated in this way was dried at 120° C. and then tableted with addition of 3% graphite. The tablets had a diameter of 3 mm and a height of 3 mm and were heat treated at 350° C. for two hours. The finished catalyst contained 25% CuO and 75% $TiO_2$, with a tap density of 1216 g/l, a BET surface area of 91 $m^2/g$ or 110656 $m^2/l$, a copper surface area of 0.3 $m^2/g$ or 365 $m^2/l$, a copper oxide crystallite size of 13.5 nm and a water uptake of 0.29 ml/g or 353 ml/l.

Catalyst D

Catalyst D was prepared as catalyst C but with addition of 15% metallic copper powder in the tableting. The finished catalyst contained 60% $TiO_2$, with a tap density of 1508 g/l, a BET surface area of 65 $m^2/g$ or 98020 $m^2/g$ a copper surface area of 0.7 $m^2/g$ or 1055 $m^2/l$, a copper oxide crystallite size of 17.5 nm and a water uptake of 0.22 ml/g or 323 ml/l.

Catalyst E (comparison)

Catalyst E was prepared by tableting $TiO_2$ powder with 3% graphite and 40% copper powder. The tablets had a diameter of 3 mm and a height of 3 mm and were heat treated at 350° C. for two hours. The finished catalyst contained 60% $TiO_2$, with a tap density of 1940 g/l, a BET surface area of 32 $m^2/g$ or 62080 $m^2/l$, a copper surface area of 0.5 $m^2/g$ or 970 $m^2/l$, a copper oxide crystallite size of 14.0 nm and a water uptake of 0.08 ml/g or 155 ml/l.

Catalyst F (comparison)

Catalyst F was prepared by precipitating a solution of copper nitrate with sodium carbonate solution. A suspension of $TiO_2$ in water was used in the recipient vessel. The precipitated material was filtered off, washed and dried at 120° C. The dried powder was calcined at 200° C. for 2 hours and then compressed with 3% graphite to 3 mm tablets. These tablets were heat treated at 330° C. for 2 hours. The finished catalyst contained 53% CuO and 47% $TiO_2$, with a tap density of 1900 g/l, a BET surface area of 74 $m^2/g$ or 140600 $m^2/l$, a copper surface area of 2.2 $m^2/g$ or 4180 $m^2/l$, a copper oxide crystallite size of 15.5 nm and a water uptake of 0.28 ml/g or 532 ml/l.

Catalyst G (comparison)

Catalyst G was prepared by precipitating a solution of copper nitrate with sodium carbonate solution. A suspension of $TiO_2$ and $Al_2O_3$ in water was used in the recipient vessel. The precipitated material was filtered off, washed and dried at 120° C. The dried powder was calcined at 200° C. for 2 hours and then compressed with 3% graphite to tablets with a diameter of 3 mm. These tablets were heat treated at 330° C. for 2 hours. The finished catalyst contained 56% CuO, 12% $Al_2O_3$ and 32% TiO2, with a tap density of 1420 g/l, a BET surface area of 77 $m^2/g$ or 109340 $m^2/l$, a copper surface area of 3.6 $m^2/g$ or 5112 $m^2/l$, a copper oxide crystallite size of 19.5 nm and a water uptake of 0.24 ml/g or 341 ml/l.

Catalyst H (comparison)

Catalyst H was prepared by precipitating a solution of copper nitrate with sodium carbonate solution. A suspension of $TiO_2$ in water was used in the recipient vessel. The precipitated material was filtered off, washed and dried at 120° C. The dried powder was calcined at 200° C. for 2 hours and then compressed with 3% graphite to tablets with a diameter of 3 mm. These tablets were heat treated at 330° C. for 2 hours. The finished catalyst contained 30% CuO and 70% $TiO_2$, with a tap density of 1760 g/l, a copper surface area of 1.3 $m^2/g$ or 2288 $m^2/l$, a copper oxide crystallite size of 15.5 nm and a water uptake of 0.20 ml/g or 352 ml/l.

Catalyst I (comparison)

Catalyst I was prepared as catalyst H but with use of a suspension of $Al_2O_3$ and water in place of an aqueous $TiO_2$ suspension in the recipient vessel for the precipitation. The finished catalyst contained 53% CuO and 47% $Al_2O_3$, with a tap density of 1200 g/l and a water uptake of 0.35 ml/g or 420 ml/l.

Catalyst J

Catalyst J according to the invention was prepared as catalyst F, merely with the addition of 20% metallic copper powder in the tableting. The finished catalyst contained about 39% $TiO_2$, with a BET surface area of 13 $m^2/g$ or 23660 $m^2/l$, a copper surface area of 1.2 $m^2/g$ or 2184 $m^2/l$, a copper oxide crystallite size of 18.5 nm and a water uptake of 0.13 ml/g or 237 ml/l.

Example 1

Hydrogenation of hydroxypivalaldehyde (HPA) to neopentyl glycol (NPG) in a Downflow Procedure (Recycle Procedure)

A mixture of 38% HPA, 38% NPG and 24% water was used as starting solution. This mixture was hydrogenated in a reactor with a volume of 200 ml in a recycle procedure with a throughput of 9.5 l/h, under a pressure of 35 bar and at a temperature of 130° C. using each of catalysts A to I. The space velocity was 0.35 $l_{HPA}/(1_{cat} \cdot h)$ in each case.

Comparison of catalyst D according to the invention with catalysts A to C and E to G (see Table 1) shows that the conversions obtained on use of D are high. The same applies to the selectivities on comparison of D with A, B, F and G. The impurities in the discharge with catalysts B to G further indicate the high chemical stability of catalyst D.

Comparison of catalyst D according to the invention with catalysts A and E to I shows the high mechanical hardness of D in the reduced moist state, and comparison of D with all the other comparison catalysts shows the high mechanical hardness of D in the oxidized state.

Comparison of catalysts D and C, which were prepared identically apart from admixture of metallic copper powder in the tableting of D, further shows the advantages of the catalyst prepared according to the invention in terms of conversion and mechanical hardness in the oxidized state.

Example 2

Hydrogenation of dimethylolbutanal (DMB) to trimethylolpropane in a Downflow Procedure with Recycling and Second Reactor A mixture of 65% DMB and 35% water was used as starting solution. This mixture was hydrogenated in a reactor with a volume of 210 ml (130 ml main reactor and 80 ml second reactor) in a recycle procedure with a throughput of 7.5 l/h and at a temperature of 120° C. (main reactor) and 130° C. (second reactor) under 90 bar using catalysts A, B, D and F, the space velocity being 0.3 $kg_{DMB}/(1_{cat} \cdot h)$.

Comparison of catalyst D according to the invention with catalysts A, B and F as in Table 2 again shows the high conversions and selectivities of D. This applies to the comparison with catalysts prepared according to the prior art with different support material (catalysts A and B) as well for the comparison with catalysts on $TiO_2$ supports tableted according to the prior art (catalyst F).

Example 3

Hydrogenation of hydroxypivalaldehyde (HPA) to neopentyl glycol (NPG) in a Downflow Procedure with Recycling and Second Reactor Example 3 was carried out as Example 2. However, the pressure of 90 bar was replaced by a pressure of 35 bar, and the space velocity was 0.45 $kg_{HPA}/(1_{cat} \cdot h)$ in place of a space velocity of 0.3 $kg_{DMB}/(1_{cat} \cdot h)$. Catalysts A, B and J were used for the hydrogenation.

Comparison of catalyst J according to the invention with A and B as in Table 3 shows that J ensures a high conversion, high selectivity and high yield.

In particular, the high chemical stability of J is noteworthy under the chosen experimental conditions which, for example, lead to dissolving of the support material of catalyst B prepared according to the prior art.

J is distinguished in comparison with catalyst A by high mechanical stability in terms of the hardness both in the reduced moist and in the oxidized state and in terms of the attrition, which makes it possible to avoid sludge formation resulting from catalyst attrition, as occurs after a prolonged running time in the case of A. All listed comparison criteria make a crucial contribution to the process being more economical on use of J.

TABLE 1 for Example 1 (downflow procedure/recycle procedure)

| Catalyst | A | B | C | D | E | F | G | H | I |
|---|---|---|---|---|---|---|---|---|---|
| Admixture of copper powder in tableting/wt. % | — | — | — | 15 | — | — | — | — | — |
| Conversion/% (from GC % areas) | 86.8 | 94.0 | 64.6 | 92.8 | 49.9 | 96.4 | 95.7 | n.m. | n.m. |
| Selectivity/% (from GC % areas) | 89.1 | 92.5 | n.m. | 92.3 | n.m. | 92.8 | 93.7 | n.m. | n.m. |
| Impurity in the discharge/ppm | n.m. | Cu: <3 Si: 6 | Cu: <3 Ti: <3 | Cu: <3 Ti: <3 | Cu: <3 Ti: <3 | Cu: <3 Ti: <3 | Cu: <3 Al: <3 Ti: <3 | n.m. | n.m. |
| Hardness/N (reduced moist state) | <15 | n.m. | n.m. | 21 | <15 | <15 | <15 | <15 | <15 |
| Hardness/N (oxidized state) | 57 | 47 | 61 | 130 | 92 | 58 | 80 | 61 | 75 |
| Attrition/wt. % (oxidized state) | 5.1 | 6.4 | 3.5 | 5.2 | 2.9 | 7.3 | 13 | 1.5 | 90 |

TABLE 2 for Example 2 (downflow procedure with recycling and second reactor)

| Catalyst | A | B | D | F |
|---|---|---|---|---|
| Admixture of copper powder in tableting/wt. % | — | — | 15 | — |
| Conversion/% (from GC % areas) | 96.2 | 99.3 | 100 | 100 |
| Selectivity/% (from GC % areas) | 73.4 | 78.4 | 83.6 | 85.6 |

TABLE 3 for Example 3 (downflow procedure with recycling and second reactor)

| Catalyst | A | B | J |
|---|---|---|---|
| Admixture of copper powder in tableting/wt. % | — | — | 20 |
| Conversion/% (from GC % areas) | 76.8 | 98.6 | 99.4 |
| Selectivity/% (from GC % areas) | 85.1 | 96.0 | 96.5 |
| Yield/% | 65.4 | 94.6 | 95.9 |
| Impurity in the discharge/ppm | Cu: n.m. Al: n.m. | Cu: <1 Si:6 (support dissolved) | Cu:<3 Ti:<3 |
| Hardness/N (reduced moist state) | <15 | n.m. | 58 |
| Hardness/N (oxidized state) | 57 | 47 | 92 |
| Attrition/wt. % (oxidized state) | 5.1 | 6.4 | 0.7 |

What is claimed is:

1. A process for the catalytic hydrogenation of a carbonyl compound or of a mixture of two or more carbonyl compounds in the presence of a catalyst in the form of tablets, said catalyst comprising an inorganic support containing $TiO_2$ and as an active component copper or a mixture of copper and at least one of the metals selected from the group of zinc, aluminum, cerium, a noble metal and a group VIII metal, wherein said catalyst additionally contains copper metal in powder form and the specific surface of said copper is at most 10 $m^2/g$.

2. The process according to claim 1, characterized in that the support material comprises a mixture of $TiO_2$ and $Al_2O_3$ or a mixture of $TiO_2$ and $ZrO_2$ or a mixture of $TiO_2$ and $Al_2O_3$ and $ZrO_2$.

3. The process according to claim 1, wherein the copper metal in powder form is present in an amount of from 5 to 40% by weight, based on the weight of said inorganic support and said active component.

4. The process according to claim 1, characterized in that the catalytic hydrogenation is conducted as a fixed bed reaction in a downflow procedure or in an upflow procedure.

5. The process according to claim 1, characterized in that the process is conducted in a recycle procedure.

6. The process according to claim 1, characterized in that there is used, as the carbonyl compound, an aliphatic aldehyde or an aliphatic hydroxy aldehyde or a mixture of two or more than two of these aldehydes.

7. Catalyst in the form of tablets, said catalyst comprising an inorganic support which contains $TiO_2$, and as an active component copper or a mixture of copper and at least one of the metals selected from the group of zinc, aluminum, cerium, a noble metal and a group VIII metal, wherein the catalyst additionally contains copper metal in powder form and has a specific surface of at most 10 $m^2/g$.

8. The catalyst according to claim 7, wherein the support material comprises a mixture of $TiO_2$ and $Al_2O_3$ or a mixture of $TiO_2$ and $ZrO_2$ or a mixture of $TiO_2$ and $Al_2O_3$ and $ZrO_2$.

9. The catalyst according to claim 7, wherein the copper metal in powder form is present in an amount of from 5 to 40% by weight, in particular in an amount of from 15 to 20% by weight, based on the weight of said inorganic support and said active component.

10. A process for the manufacture of a catalyst according to claim 7 in the form of tablets, which process comprises the steps of mixing the components and tabletting the mixture, wherein the catalyst material is formed to tablets after adding copper metal in powder form.

11. The process according to claim 1, wherein the copper metal in powder form is present in an amount of from 15 to 20% by weight, based on the weight of said inorganic support and said active component.

* * * * *